United States Patent [19]

Rhodes

[11] 4,041,944
[45] Aug. 16, 1977

[54] BODY FLUID TRANSFUSION AND DISPLACEMENT APPARATUS AND METHOD

[76] Inventor: William A. Rhodes, 4421 N. 13th Place, Phoenix, Ariz. 85014

[21] Appl. No.: 597,501

[22] Filed: July 21, 1975

[51] Int. Cl.² ............... A61M 1/02; A61M 5/14
[52] U.S. Cl. ............... 128/214 B; 128/214 F; 128/278; 128/DIG. 12; 222/386.5
[58] Field of Search ........... 128/214 R, 214 B, 214 E, 128/214 F, 214 D, DIG. 12, DIG. 13, DIG. 3, 278; 222/95, 386.5, 395; 137/99, 564.5

[56] References Cited

U.S. PATENT DOCUMENTS

| | | | |
|---|---|---|---|
| 1,473,979 | 11/1923 | Simmons | 128/DIG. 12 |
| 1,937,566 | 12/1933 | Hanafin et al. | 128/214 B UX |
| 1,946,474 | 2/1934 | Banks et al. | 137/564.5 X |
| 2,483,924 | 10/1949 | Moulinier | 128/278 UX |
| 2,932,317 | 4/1960 | Klosse | 137/564.5 |
| 3,032,037 | 5/1962 | Huber | 128/DIG. 12 |
| 3,044,663 | 7/1962 | Norton et al. | 128/214 F UX |
| 3,166,096 | 1/1965 | Lang | 222/386.5 X |
| 3,199,511 | 8/1965 | Kulick | 222/395 X |
| 3,256,908 | 6/1966 | Mann | 137/564.5 X |
| 3,291,151 | 12/1966 | Loken | 128/214 B X |
| 3,483,867 | 12/1969 | Markovitz | 128/214 R |
| 3,496,878 | 2/1970 | Hargest et al. | 128/214 R X |
| 3,511,238 | 5/1970 | Von Wrangell | 128/214 R |
| 3,593,533 | 7/1971 | Washington | 222/386.5 X |
| 3,720,230 | 3/1973 | Miller et al. | 137/564.5 |

FOREIGN PATENT DOCUMENTS 243,785   10/1969   U.S.S.R. ............... 128/2 A

Primary Examiner—Clifford D. Crowder

[57] ABSTRACT

A body fluid transfusion and displacement apparatus and method wherein the transfusion of blood, saline solutions or the like, may be maintained at an equilibrium in the patient volumetrically by means of apparatus which transfers blood out of the patient and into the patient as exactly the same volumetric rate; the apparatus having a pair of hollow needles, one of the needles being inserted into an artery, and the other of the needles being inserted into a vein; and wherein a pair of containers are separated by a deflectable member such that fluid transferred out of the patient displaces the deflectable member adjacent to one container and forces it into an area of the other container whereby the blood displaced from the patient positively acts against the deflectable member to control the delivery of fluid into the patient; the apparatus also having modifications of the flexible member, as well as a reversible pump and a vent valve and additionally, the apparatus is related to a method of transfusion displacement of body fluids relative to a patient.

5 Claims, 4 Drawing Figures

BODY FLUID TRANSFUSION AND DISPLACEMENT APPARATUS AND METHOD

BACKGROUND OF THE INVENTION

The foregoing prior art teaches the employment of various means for blood transfusion or the transfusion of body fluids relative to a human patient. However, the various apparatus and methods do not provide for the concurrent removal and replacement of blood relative to a patient wherein the amount of blood being removed from the patient is almost exactly equal to the amount of blood being injected into the patient so that the patient is not upset in any way by any differential in the volumetric displacement of fluids relative to his body. Accordingly, the prior art lacks precise control of the removal of fluids from a patient's body relative to the precise replacement of the fluids on a volumetric equality basis.

Many of the prior art devices have alternating mechanism which alternately withdraws a small portion of blood from the patient and then subsequently replaces it and thus, such means may be cycled many times depending upon the amount of fluid or blood to be displaced and transfused.

This system however, does not permit the concurrent equality volumetrically of the displacement and transfusion of blood or other body fluids relative to a patient either into or out of a vein concurrently relative to the reciprocal displacement or transfusion in relation to an artery.

SUMMARY OF THE INVENTION

The present invention comprises a novel means and method for concurrently and equally displacing and transfusing body fluids relative to a patient by coupling a hollow needle into a view concurrently with the coupling of a needle into the artery of the patient and whereupon a pair of containers communicating with the respective needles receive and dispense the fluids relative to the patient and whereby a flexible member between the containers is deflected such that fluid displaced from the patient exactly equals fluid transfused into the patient.

The invention also comprises a pump in communication with one of the containers which operates at a very slow rate compatible with the normal displacement of blood from a blood vessel of a patient through a hollow needle inserted therein. Additionally, the invention comprises means for venting all of the pneumatic fluids from the containers when primed to transfuse fluid into either the vein or artery of a patient while concurrently removing fluid from the patient through either a vein or an artery of the patient.

The invention comprises a novel method which affords equality of volumetric transfusion and displacement of body fluids relative to the patient so that the volumetric fluid content of the patient is not disturbed.

The invention comprises more than one species of the apparatus in which a pair of containers are separated by flexible means which is deflected to enlarge one of the containers while reducing the other of the containers proportionately so that fluids may be transfered into one of the containers and out of the other container at exactly the same volumetric displacement and rate.

A pump in connection with one of the containers operates at a very low rate and transfers blood to or from one of the containers in accordance with a conduit connected therewith which may be coupled to either an artery or a vein of the patient.

Accordingly, it is an object of the invention to provide a novel method for transfusing and displacing blood or other body fluids relative to the patient, wherein: one hollow needle is placed in a vein of the patient and one hollow needle is placed in an artery of the patient and these needles communicate with the respective conduits which communicate with respective separate chambers separated by a flexible means which deflects to reduce the volume of one container concurrently and volumetrically proportional while the other of the containers is filled with blood or other body fluids displaced from the patient.

Another object of the invention is to provide a novel apparatus for transfusion displacement of blood or other body fluids relative to a patient, wherein: the blood or other fluids may be injected into the patient and concurrently, fluids may be removed from the patient at a common rate and at the same volumetric displacement, so that the volumetric fluid content of the patient is not disturbed or varied.

Another object is to provide a novel means or apparatus, as aforementioned, wherein: the priming of the containers is accompanied by the use of vent valves which are adapted to purge the containers of all pneumatic fluids or bubbles preliminary to the transfusion and displacement of body fluids such as blood or saline solutions relative to the patient through the blood vessels including at least one vein and at least one artery.

Further objects and advantages of the invention may be obvious with reference to the following specification, accompanying drawings and appended claims.

DESCRIPTION OF THE PREFERRED EMBODIMENTS

Figure 1:
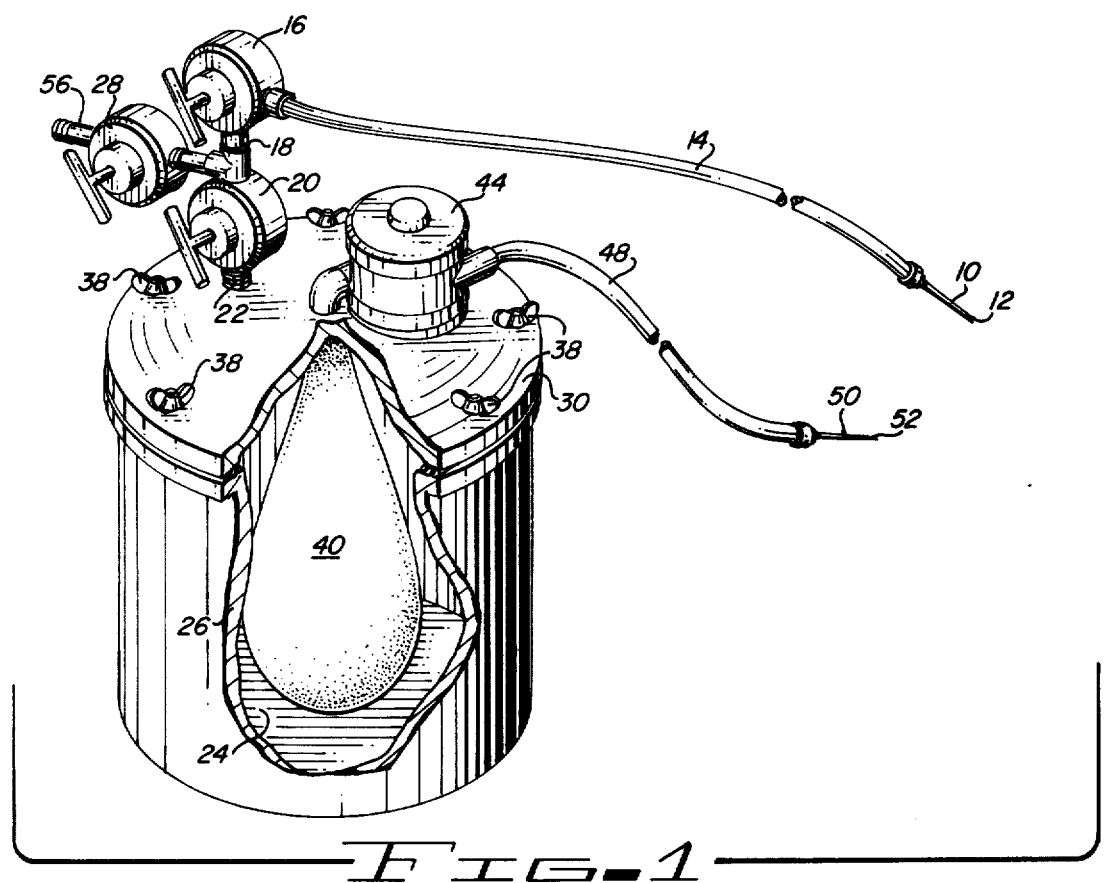
FIG. 1 is a prospective view of the apparatus of the invention used for the transfusion displacement of body fluids relative to a patient and showing portions thereof broken away and in sections to amplify the illustration.

The apparatus, in accordance with the present invention, comprises a first hollow needle 10 having a pointed end 12 which may be inserted into either a vein or an artery of a patient. This hollow needle 10 communicates with a hollow flexible conduit 14 which in turn communicates with a valve 16 and a short conduit 18 couples the valve 16 with another valve 20 which communicates with a short connection 22 with the interior 24 of a container 26.

A third valve 28 communicates with the conduit portion 18 between the valves 16 and 20 and this valve 28 serves as a vent to atmosphere for venting bubbles or pneumatic fluids from the container 24 as will be hereinafter described in detail. The container 26 is provided with a cover 30 having an elevated area 32 into which the short conduit portion 22 communicates. A sealing gasket 34 is disposed between the cover 30 and a flanged upper open end 36 of the container 26 so as to provide for sealable connection of the cover 30 with the container 26 and wing-bolt fixtures 38 are disposed to clamp the cover 30 tightly onto the flanged open end portion of the container 26.

Disposed in the container 26 is a deflectable and/or collapsable and distendable bag 40 which is sealingly extended through the cover 30 at 42 and communicating with this collapsible and distendable bag 40 is a pump 44 having an output conduit 46 which communicates with a conduit 48 as shown best in FIG. 1 of the drawings. This conduit 48 communicates with a second hollow needle 50 having a sharp open end 52 adapted to be inserted into a blood vessel of the patient, either an artery or a vein.

It will be seen that the valve 16 is provided with an inlet fixture 54 which communicates with the conduit 14 while the valve 28 is provided with a fixture 56 adapted to vent pneumatic fluids or bubbles therefrom in the direction of the arrow 58 and into any suitable waste or disposal area.

Figure 2:
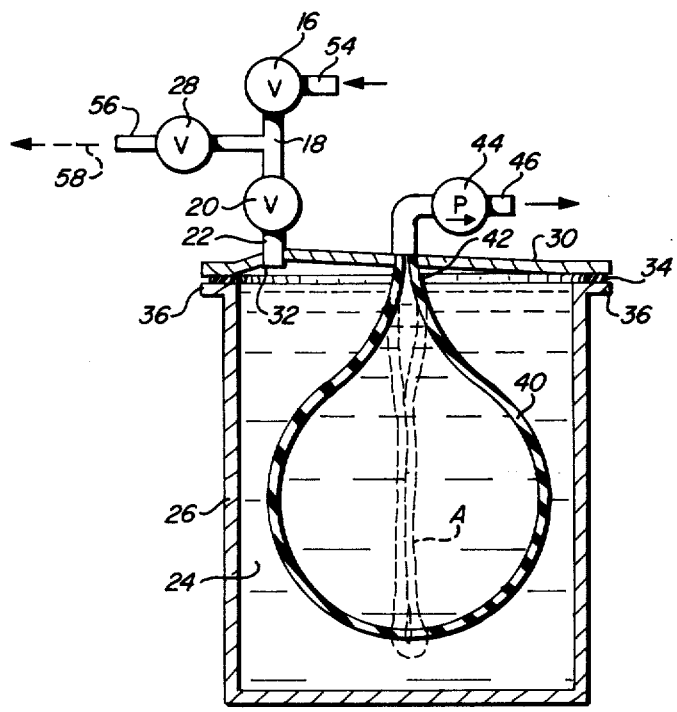
FIG. 2 is a vertical sectional view of portions of the apparatus as shown in FIG. 1 and showing by broken lines the deflection of a flexible container means in a relatively rigid container.

It will be understood that the disclosure FIG. 2 is somewhat diagramatic in relation to the disclosure of the pump which is mounted on the cover 30 substantially as shown in FIG. 1 of the drawings.

An example of the operation of the apparatus as shown in FIGS. 1 and 2 of the drawings is as follows. The distendable and collapsible bag 40 is first partially filled with a fluid, preferably a saline fluid, and this is done by pumping the fluid into the interior of the bag 40 by means of the pump 44. Then the pump is reversed so as to pump the saline solution out of the bag together with any air trapped therein until the bag is collapsed substantially as shown by broken lines A in FIG. 2 of the drawings. The bag is thus completely purged of bubbles and leaves normal saline solution only in the bag and the conduit 48 as well as the needle 50.

With the bag or container 40 thus collapsed, the interior 24 of the container 26 is filled with water or normal saline solution. The cover 30 is then clamped tightly on the flanged structure 36 of the container by the fixtures 38 against the gasket 34 which may be any suitable gasket such as an O-ring so as to seal the cover 30 with the container 26. Valve 28 is then closed and valve 16 and 20 are opened and normal saline or other suitable fluid is primed into the conduit 14. Valve 16 is then closed and valve 28 is opened and the conduit 14 is now primed with normal saline or other suitable fluid. The needle 50 is then inserted into a vial of new blood and the valve 28 is opened. The pump 44 is reversed which pumps blood into the bag 40 and expands into the interior 24 of the container 26 displacing saline solution therefrom and letting air bubbles or pneumatic fluids out through the valve 28 and the outlet 56 thereof. The pump is then stopped and the valve 28 is then closed.

The needle 50 is then inserted into an artery or a vein and the needle 10 is inserted into a respective artery or a vein and valve 16 is opened and the pump 44 is started to operated in a clockwise direction to deliver fluid from the interior of the bag or container 40 outward through the needle 50.

It will be understood that if the needle 50 is inserted in a vein, the needle 10 is inserted in an artery and vice versa, depending on the desired mode of operation followed by the particular physician.

Fresh blood or other fluids are delivered into the patient through the needle 52 and this fluid is exactly displaced volumetrically and concurrently by blood and/or fluids flowing out from the patient through the needle 10 and into the container interior 24. This fluid passing into the interior of the container 24 is positively filled in against the deflectable wall of the bag 40 which concurrently collapses due to the removal of fluid therefrom by means of the pump 44. Flow in both needles 10 and 50 and the respective conduits 14 and 48 automatically ceases when the bag 40 is fully collapsed. At this time the pump 44 is stopped and the needles 10 and 50 are removed from the patient.

Accordingly, it will be appreciated that the method of the invention comprises a concurrent transfusion and displacement of blood or other body fluid relative to a patient and this is accomplished by at least one hollow needle in a vein and at least one hollow needle in an artery of a patient, and conduits coupled to the respective needles and communicating with separate containers wherein a collapsable or deflectable barrier separates the chambers so that while fluid is being transfused into the patient, the fluid removed from the patient acts against the deflectable structure separating the containers so as to exactly match the fluids being transfused and displaced relative to the patient. In this manner, body fluids may be transfused into and displaced from the patient concurrently at exactly the same rate and volumetric proportions so that the actual volumetric fluid content of the patient is not changed or distrubed.

Figure 3:
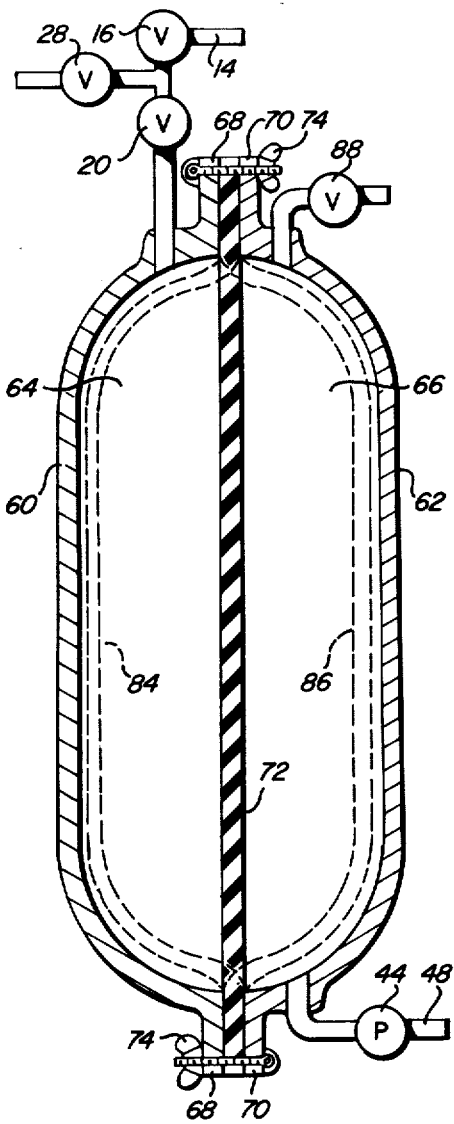
FIG. 3 is a sectional view similar to FIG. 2 showing a modification of the apparatus.
Figure 4:
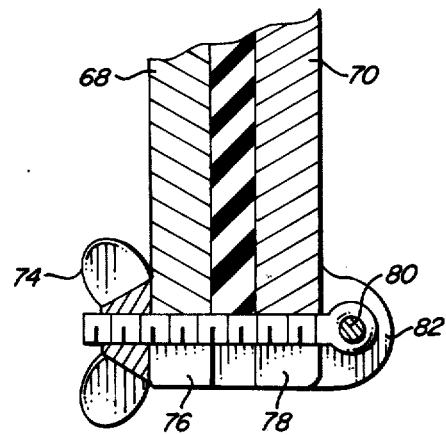
FIG. 4 is an enlarged fragmentary sectional view of a portion of the the sketch as shown in FIG. 3 illustrating in detail the container holding and clamping mechanism.

In the modification of the invention as shown in FIG. 3, a first container 60 and a second container 62 comprise respective container displacement area 64 and 66 respectively. The containers 60 and 62 are dislike members having respective peripheral flanges 68 and 70 which are clamped together sealingly at opposite sides of the flexible diaphram 72 which separates the container spaces 64 and 66. Fluids are transfused and displaced relative to the apparatus shown in FIG. 3 in a manner similar to that disclosed in FIG. 1 wherein the conduits 14 and 48 are similar and the pump 44 as well as the valves 16, 20 and 28 operate in a similar manner. The container 60 and 62 at their flanges 68 and 70 are held together by wing-bolts 74 which extend through respective slots 76 and 78 in the peripheries of the flanges 68 and 70 as shown in FIG. 4 and each respective wing-bolt 74 is provided with a pivoted end A mounted on a pivot boss 82 on the container member 62 and the wing-bolt 74 in each instance is pivotal through the slots 76 and 78 into and out of the position shown in FIG. 4 so that the container 60 and 62 may be readily disassembled relative to the flexible diaphram 72 which may be deflected into either of the broken line positions 84 or 86 depending upon the operation of the apparatus as desired.

A separate fluid vent valve 88 may be disposed in the upper portion of the container 62 or the pump 44 may be disposed at such a location as desired depending upon the design perimeters of the apparatus.

It will be obvious to those skilled in the art that various modifications of the invention may be resorted to without departing from the spirit of the invention.

I claim:

1. A means for displacing and transfusing body fluids relative to a patient comprising: a substantially rigid container; a distensible and collapsible container disposed in said substantially rigid container; a first fluid conduit communicating with the interior of said substantially rigid container; a second fluid conduit communicating with the interior of said distensible and collapsible container; first and second hollow needles adapted to be inserted into a patient's blood vessels; said first and second needles being coupled to and in communication with respective ones of said conduits and the interior of said first and second fluid containers respectively; and reversible means communicating with one of said conduits and adapted to move fluid into and out of a respective one of said containers; said pump communicating with said second fluid conduit; valve means disposed and adapted for purging air bubbles out of said substantially rigid container; said valve means comprises three valves; the first one of said valves communicating directly with the interior of said substantially rigid container; a second valve communicating with said first valve; said second valve communicating with said first fluid conduit; and a third valve communicating between said first and second valve for venting bubbles or the like.

2. The invention as defined in claim 1, wherein: said substantially rigid container is provided with a movable and sealable cover; said distensible and collapsible container carried by said cover.

3. The invention as defined in claim 2, wherein: said pump is carried by said cover.

4. The invention as defined in claim 2, wherein: said valve means is carried by said cover.

5. A means for transfusing and displacing body fluids relative to a patient comprising: a first container; a second container; one of said containers having movable means deflectable into the other of said containers whereby an amount of fluid entering one of said containers displaces an equal amount of fluids from the other of said containers; and first and second fluid conduit means communicating with the interiors of said first and second containers; first hollow needle means coupled to one of said conduit means for insertion into a first blood vessel of a patient; second needle means coupled to the other of said fluid conduit means for insertion into a second blood vessel of a patient; and a pump communicating with one of said containers and one of said fluid conduit means; valve means adapted for purging air bubbles out of one of said containers; said valve means comprises three valves; a first one of said valves communicating directly with the interior of one of said containers; a second valve communicating with said first valve; said second valve communicating with said first fluid conduit; and a third valve communicating between said first and second valves for venting bubbles or the like.

* * * * *